United States Patent
Jang et al.

(10) Patent No.: US 12,421,485 B2
(45) Date of Patent: Sep. 23, 2025

(54) CELL CULTURE SHEET ASSEMBLY FOR LARGE-CAPACITY INCUBATOR, AND LARGE-CAPACITY INCUBATOR COMPRISING SAME

(71) Applicant: AMOGREENTECH CO., LTD., Gimpo-si (KR)

(72) Inventors: Seon Ho Jang, Seoul (KR); Hee Sung Park, Seoul (KR); Kyung Gu Han, Goyang-si (KR); Dong Sik Seo, Incheon (KR); Song Hee Koo, Gimpo-si (KR); Ji Young Kim, Gimpo-si (KR); Hyo Jung Lee, Seoul (KR); Su Yeon Lee, Gimpo-si (KR); In Yong Seo, Seoul (KR); Seoung Hoon Lee, Paju-si (KR); Chan Kim, Gwangju (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 1031 days.

(21) Appl. No.: 17/293,993

(22) PCT Filed: Nov. 14, 2019

(86) PCT No.: PCT/KR2019/015568
§ 371 (c)(1),
(2) Date: May 14, 2021

(87) PCT Pub. No.: WO2020/101399
PCT Pub. Date: May 22, 2020

(65) Prior Publication Data
US 2022/0002651 A1   Jan. 6, 2022

(30) Foreign Application Priority Data
Nov. 14, 2018  (KR) ........................ 10-2018-0140010

(51) Int. Cl.
*C12M 1/12*   (2006.01)

(52) U.S. Cl.
CPC ............ *C12M 25/14* (2013.01); *C12M 25/02* (2013.01); *C12N 2533/30* (2013.01); *C12N 2535/00* (2013.01)

(58) Field of Classification Search
None
See application file for complete search history.

(56) References Cited

U.S. PATENT DOCUMENTS 3,729,382 A * 4/1973 Roz .................. C12M 23/10
                                                                   435/309.4
4,228,243 A * 10/1980 Iizuka ................ C12M 23/34
                                                                   435/294.1

(Continued)

FOREIGN PATENT DOCUMENTS

JP    2007089448 A  *  4/2007  ............ C12M 23/04
JP    2012213390 A  *  11/2012  ............ C12M 25/02

(Continued)

OTHER PUBLICATIONS

Machine Translation of KR 20170008024 A, Hwang Chang Mo, Jan. 23, 2017 (Year: 2017).*

(Continued)

*Primary Examiner* — Henry H Nguyen
(74) *Attorney, Agent, or Firm* — ROTHWELL, FIGG, ERNST & MANBECK, P.C.

(57) ABSTRACT

A cell culture sheet assembly for a large-capacity incubator, wherein a plurality of cell culture sheets are disposed to be spaced apart at predetermined intervals in a direction perpendicular to a main surface, in which each cell culture sheet has an area of 100 cm$^2$ or more, a thickness of 200 to 800 μm, and a bending depth of 0.5 cm or less. Even when the culture sheets are closely placed in a limited volume of space, there is little sagging or shape deformation in a (Continued)

specific direction to prevent contact with adjacent culture sheets, thereby preventing a decrease in cell culture volume due to dead space. Because the flow of a cell culture fluid due to the occurrence of contact can be minimized or prevented, the cell culture sheet assembly is suitable for large-capacity incubators and can be widely applied to the cell culture industry.

9 Claims, 5 Drawing Sheets

Specification includes a Sequence Listing.

(56) References Cited

U.S. PATENT DOCUMENTS

| | | | |
|---|---|---|---|
| 8,071,382 B2 | 12/2011 | Bae et al. | |
| 2003/0157709 A1 | 8/2003 | DiMilla et al. | |
| 2010/0190249 A1 | 7/2010 | Kruse et al. | |
| 2010/0304472 A1 | 12/2010 | Kim et al. | |
| 2011/0151565 A1 | 6/2011 | Hase et al. | |
| 2014/0087465 A1 | 3/2014 | Yoshikawa et al. | |
| 2015/0017714 A1* | 1/2015 | Kabaha | B04B 5/04 435/297.3 |
| 2017/0108420 A1* | 4/2017 | Burns | G01N 3/42 |
| 2017/0229043 A1* | 8/2017 | Huh | G09B 23/32 |
| 2020/0318049 A1 | 10/2020 | Koo et al. | |

FOREIGN PATENT DOCUMENTS

| | | | |
|---|---|---|---|
| JP | 2013138691 A | | 7/2013 |
| JP | 2015012863 A | | 1/2015 |
| JP | 2017046676 A | * | 3/2017 |
| JP | 2017085959 A | | 5/2017 |
| KR | 10-2006-0071890 A | | 6/2006 |
| KR | 10-2009-0056667 A | | 6/2009 |
| KR | 10-2017-0008024 A | | 1/2017 |
| KR | 10-2017-0135769 A | | 12/2017 |
| WO | 2012/144624 A1 | | 10/2012 |

OTHER PUBLICATIONS

Machine translation of KR 20170135769 A, Koo Song Hee, Dec. 8, 2017 (Year: 2017).*
Machine translation of JP 2012213390 A, Oyabu Yoshimi Nov. 8, 2012 (Year: 2012).*
Machine translation of JP2017046676A, Watanabe Rie, Mar. 9, 2017 (Year: 2017).*
Translation of JP 2007089448 A, Ikari Takaomi, Apr. 12, 2007 (Year: 2007).*
International Search Report cited in PCT/KR2019/015568 dated Mar. 4, 2020, 2 pages.

* cited by examiner

【FIG. 1】
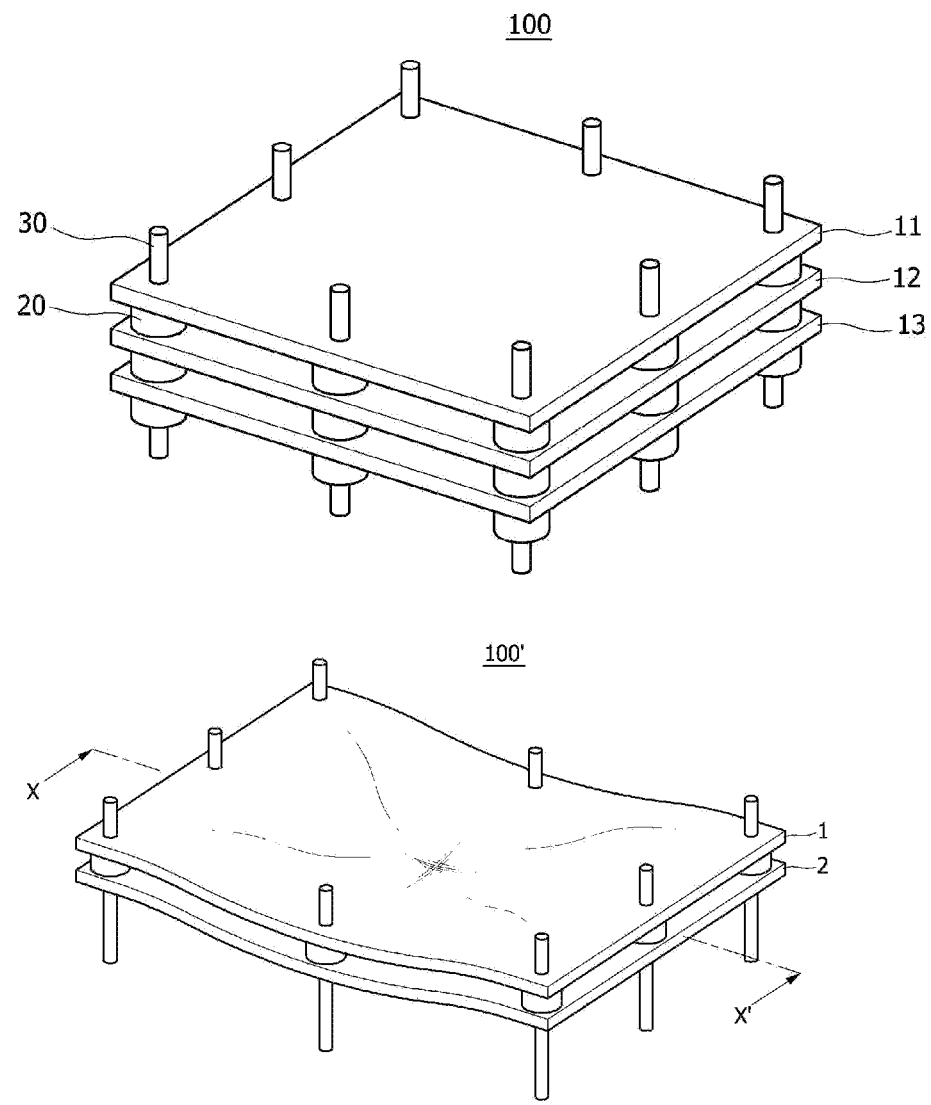
【FIG. 2】
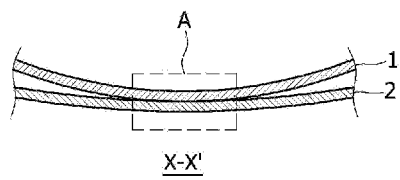

[FIG. 3]
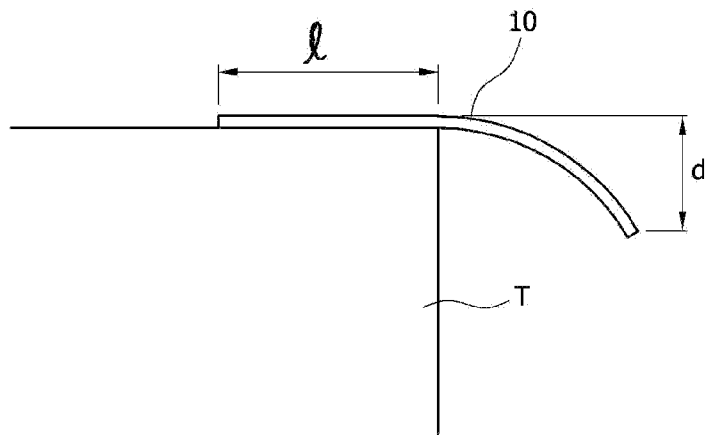
[FIG. 4]
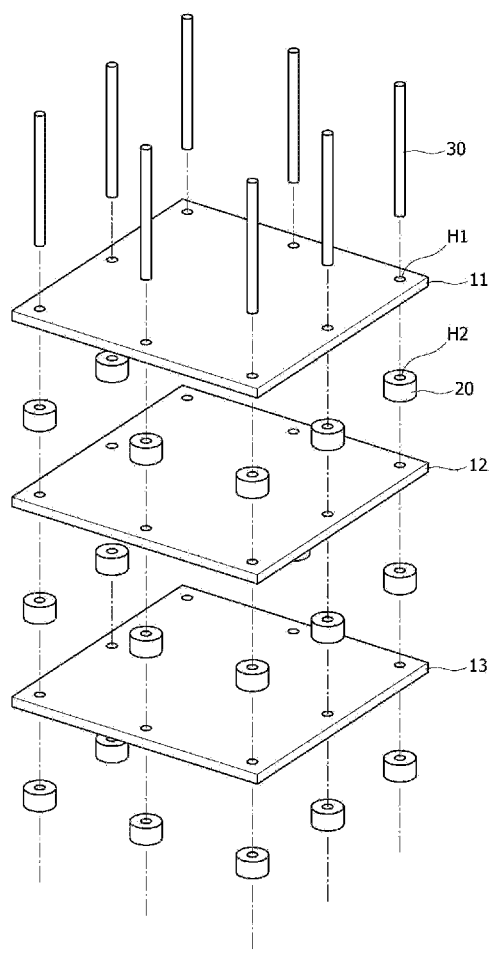

[FIG. 5]
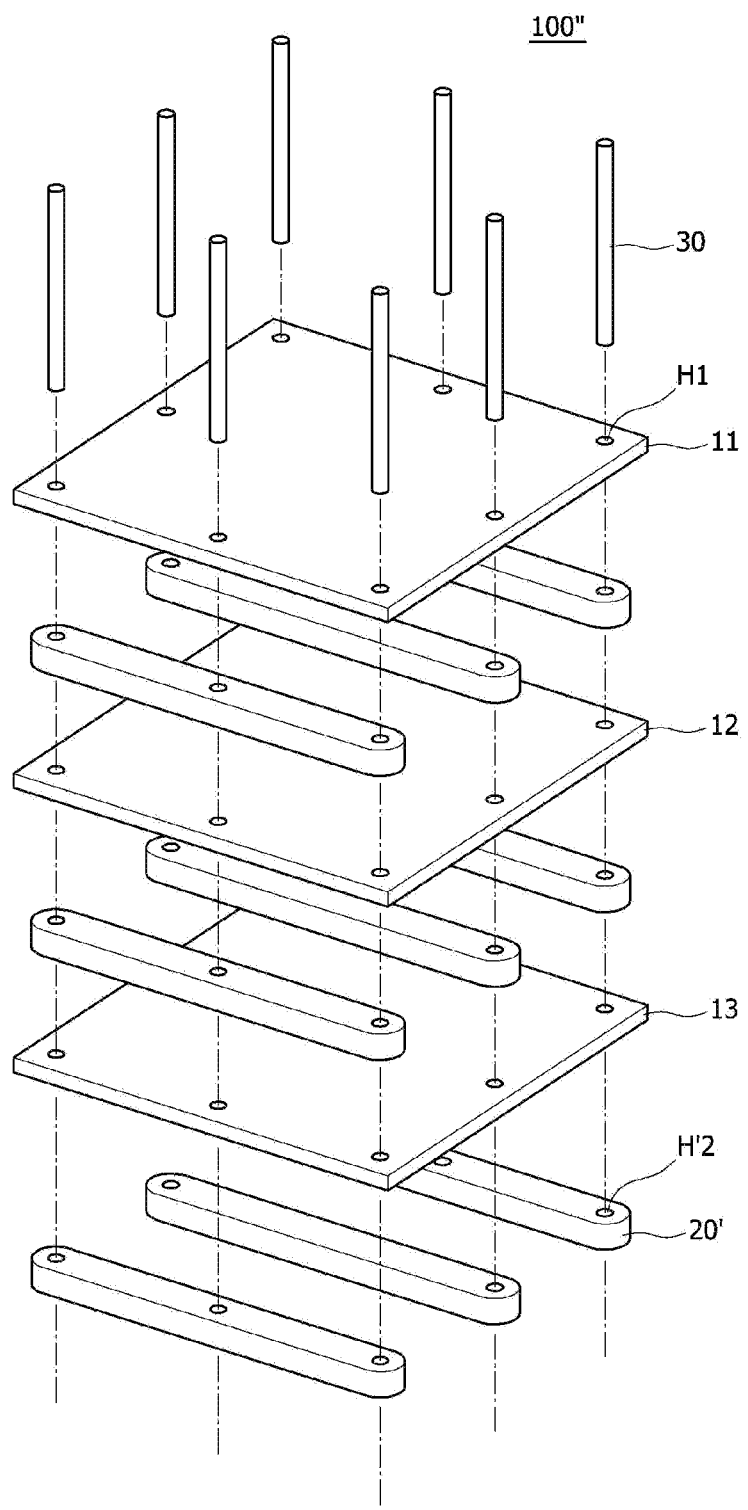

[FIG. 6]
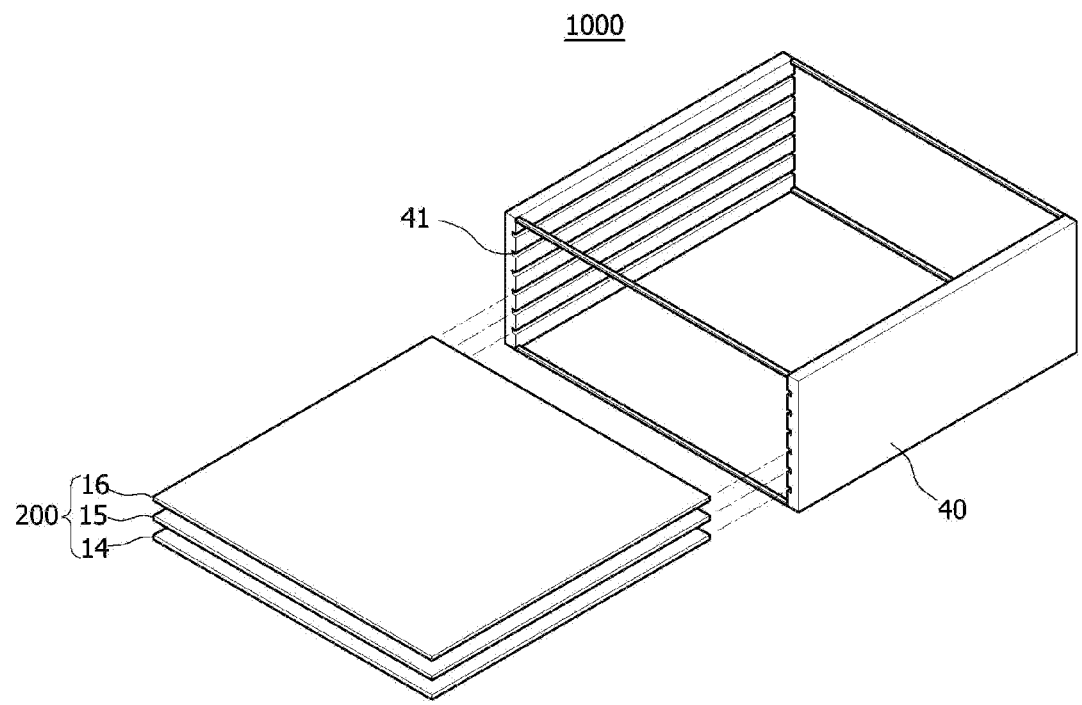
[FIG. 7]

【FIG. 8】
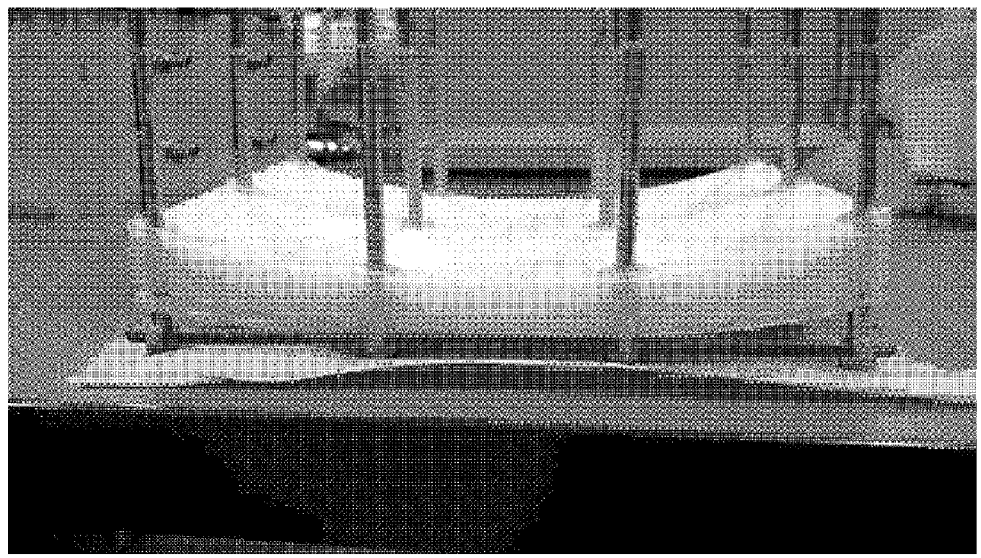
【FIG. 9】
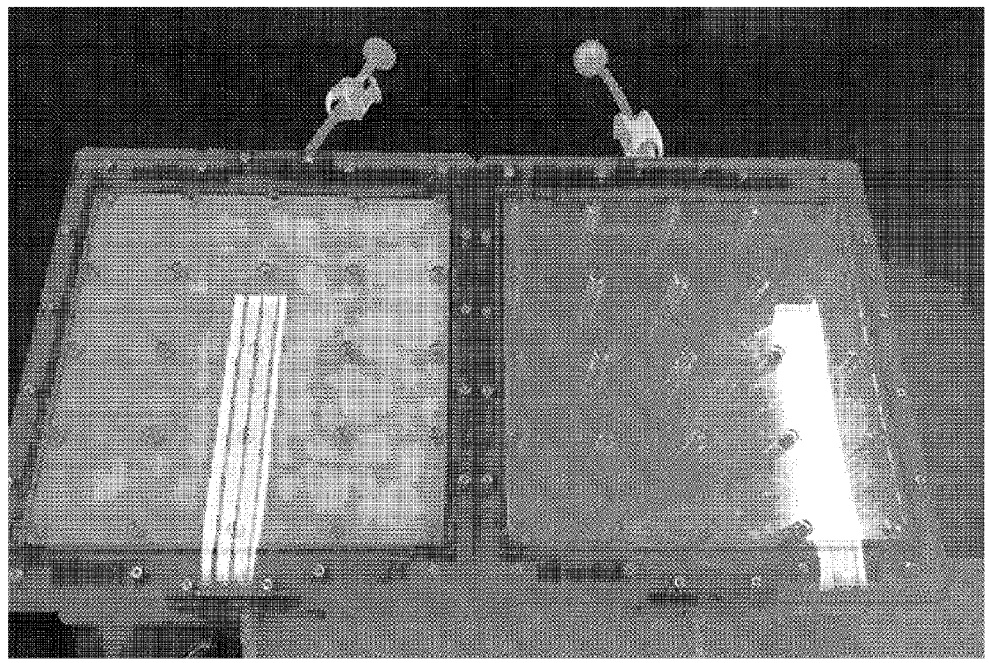

CELL CULTURE SHEET ASSEMBLY FOR LARGE-CAPACITY INCUBATOR, AND LARGE-CAPACITY INCUBATOR COMPRISING SAME

CROSS REFERENCE TO RELATED APPLICATION

This application is a 35 U.S.C. 371 National Phase Entry Application from PCT/KR2019/015568, filed Nov. 14, 2019, which claims the benefit of Korean Patent Application No. 10-2018-0140010 filed on Nov. 14, 2018, the disclosures of which are incorporated herein in their entirety by reference.

The instant application contains a Sequence Listing which has been submitted via EFS-Web and is hereby incorporated by reference in its entirety. Said Sequence Listing, created on May 13, 2021, is named 4669-161 ST25.TXT and is 13 kilobytes in size.

TECHNICAL FIELD

The present invention relates to a cell culture sheet assembly, and more specifically, to a cell culture sheet assembly for a large-capacity incubator, and a large-capacity incubator comprising the same.

BACKGROUND ART

Recently, as the use of cultured cells for disease treatment has expanded, interest in and research in cell culture has increased. Cell culture is a technique for collecting cells from living organisms and culturing the cells in vitro, and cultured cells may be used to treat various diseased by differentiating the cultured cells into various tissues of the body such as skin, organs, and nerves to be transplanted into the human body, or differentiating the cultured cells in a state before being differentiated to achieve both engraftment and differentiation.

In order to transplant cells cultured for the treatment of a disease into the human body, it is required that the number of target cells be cultivated in an amount exceeding the laboratory level. However, since it is difficult for cells to proliferate in three dimensions instead of two dimensions, culturing cells using a large-area scaffold in order to obtain a large number of cells is inevitable.

However, considering that a cell incubator has a limited volume, there is a limitation in increasing the area of a scaffold, and it is required that the scaffold is provided so as to have as much specific surface area as possible in a cell incubator having a limited volume.

As a method for solving these problems, it can be considered that a plurality of plate-shaped scaffolds are spaced apart at predetermined intervals and arranged in a limited culture space. In this case, it is advantageous that the scaffold has a thin thickness such that a large number of scaffolds can be stacked within a limited height while the scaffold has a maximum area within a range allowed by the culture space.

However, when the area and thickness of the scaffold become large and thin, respectively, the influence of its own weight becomes large, such that the central portion of the scaffold on which the side portion is supported may be concavely depressed and sag downward. Further, when the scaffold is wetted with a cell culture fluid, there is a risk that the scaffold may sag more markedly. In this case, there are problems in that due to sagging, contact may occur between the lower surface of a scaffold and the upper surface of the scaffold disposed below the scaffold, and the portion where contact occurs becomes a dead space in which cells cannot proliferate and the volume for cell culture is reduced.

In addition, a cell culture fluid is located between the scaffolds stacked at predetermined intervals, but the sagging of the scaffold narrows the interval between the scaffolds, thereby obstructing or blocking the flow of the cell culture fluid, so there is a risk that the cell culture efficiency may be significantly reduced.

Furthermore, when mechanical strength is not supported enough to cause sagging, the flowing cell culture fluid may induce continuous shaking of the scaffold, and such shaking has a problem of making stable cell culture difficult.

Therefore, there is an urgent need for studies on a cell culture scaffold capable of solving the above-described dead space problem even when a large-area cell culture scaffold is provided and stacked at a predetermined interval, and stably cultivating cells because the separation distance between the scaffolds is continuously maintained, and thus there is little shaking of the scaffold even in the flow of the cell culture fluid without obstructing the flow of the cell culture fluid.

DISCLOSURE

Technical Problem

The present invention has been devised in consideration of the above-described points, and an object of the present invention is to provide a cell culture sheet assembly for a large-capacity incubator, which can prevent the occurrence of contact with other adjacent culture sheets or minimize or prevent the obstruction of the flow of a cell culture fluid because there is little sagging or shape deformation in a specific direction even when a large number of the cultures sheet are closely placed in a limited volume of space, and which can stably cultivate cells with little shaking despite the flow of the cell culture fluid; a cell culture sheet for a large-capacity incubator, which constitutes the same; and a large-capacity incubator including the same.

Technical Solution

To solve the above-described problems, the present invention provides a cell culture sheet assembly for a large-capacity incubator, in which a plurality of sheets are disposed to be spaced apart at predetermined intervals in a direction perpendicular to the main surface, and the cell culture sheet has an area of 100 cm$^2$ or more and a bending depth of 0.5 cm or less.

According to one embodiment of the present invention, a vertical distance between adjacent cell culture sheets may be 0.1 to 20 mm.

Further, the cell culture sheet may include any one or more of a fiber web and a film.

In addition, the cell culture sheet may have a thickness of 200 to 800 μm.

Furthermore, the cell culture sheet may include any one or more components selected from the group consisting of polystyrene (PS), polyester, polyethersulfone (PES), polyvinylidene fluoride (PVDF), polydimethylsiloxane (PDMS), polyamide, polyimide, polyethylene, and polypropylene.

Further, the cell culture sheet may include a fiber web having a basis weight of 1 to 20 g/m$^2$, which is formed of fibers having an average diameter of 10 nm to 1.5 μm.

In addition, the cell culture sheet may have a bending depth of 2.6 cm or less measured after being allowed to stand at 121° C. and 1.15 atm for 1 hour.

Furthermore, the cell culture sheet has a predetermined curvature in any one direction of a width direction or longitudinal direction, and may have a radius of curvature of 0.1 to 0.5 mm.

Further, the surface of the cell culture sheet may be provided with a physiologically active component having a function of promoting any one or more of cell attachment, migration, proliferation and differentiation.

In addition, the cell culture sheet may be a laminate in which a fiber web having a thickness of 1 to 10 mm and a film on one surface of the fiber web are integrated.

Furthermore, the present invention provides a cell culture sheet provided in a large-capacity incubator having a plurality of sheets disposed to be spaced apart at predetermined intervals in a direction perpendicular to the main surface in an internal space, in which the cell culture sheet has an area of 100 $cm^2$ or more and a bending depth of 0.5 cm or less.

Further, the present invention provides a large-capacity incubator including a housing having an internal space and the cell culture sheet assembly according to the present invention accommodated in the internal space.

According to one embodiment of the present invention, provided is a large-capacity incubator in which the cell sheet assembly further includes first holes passing through at predetermined intervals along the edge of each cell culture sheet and a spacer provided with a second hole, and a support having a diameter corresponding to the first holes and the second hole, and the spacer is disposed between adjacent cell culture sheets such that the first hole and the seconds hole of the cell culture sheet correspond to each other, and the support is inserted so as to pass through the first hole and the second hole disposed to correspond to each other.

In addition, slits formed to be spaced apart at predetermined intervals may be provided on both facing inner surfaces of a housing such that each cell culture sheet in a cell culture sheet assembly is inserted along the inner side surface of the housing and fixed.

Furthermore, the present invention provides a tissue engineering transplant including the cell culture sheet assembly according to the present invention and cells cultivated on each cell culture sheet in the cell culture sheet assembly.

Hereinafter, the terms used in the present invention will be described.

As used herein, the "extracellular matrix (ECM)" refers to a matrix that surrounds the outside of cells, in which the matrix is present between cells and has a network structure mainly including proteins and polysaccharides.

The "motif" of the present invention is a peptide which is included in extracellular matrix proteins, membrane proteins, and the like which play an important role in cell attachment, migration, proliferation, differentiation and the like and includes an amino acid sequence capable of structurally/functionally interacting with a receptor provided so as to pass through the surface or membrane of the cell membrane, and includes all of those separated in cells or artificially produced using a gene cloning technique.

Advantageous Effects

According to the present invention, even when a plurality of large-area cell culture sheets are closely spaced apart and placed in a limited volume of space, there is little sagging or shape deformation in a specific direction as the cell culture sheet satisfies the properties according to the present invention, so that as a dead space due to the occurrence of contact with other adjacently disposed culture sheets is minimized or prevented, there is an advantage in that a cell culture area initially designed can be maximally used for cell culture. Further, since the flow of a cell culture fluid located between adjacently disposed cell culture sheets can be continuously and smoothly maintained, a fresh cell culture fluid can be provided to cells regardless of the position of the large-area cell culture sheet, and it is advantageous for constantly maintaining the carbon dioxide concentration and the like of the cell culture fluid regardless of the position in a large-capacity incubator. Furthermore, even when there is a flow of the cell culture fluid, cells can be stably cultivated because shaking hardly occurs, so that the cell culture sheet can be widely applied to the cultivation of a large capacity of cells.

DESCRIPTION OF DRAWINGS

FIG. 1 is a perspective view of a cell culture sheet assembly according to one embodiment of the present invention.

FIG. 2 illustrates a perspective view of a cell culture sheet assembly according to the comparative example of the present invention, and a partial cross-sectional view along the X-X' boundary line.

FIG. 3 is a schematic view illustrating a method of measuring the bending depth of a cell culture sheet according to the present invention.

FIG. 4 is an exploded perspective view of FIG. 1.

FIG. 5 is an exploded perspective view of a cell culture sheet assembly according to one embodiment of the present invention.

FIG. 6 is an exploded perspective view of a large-capacity incubator according to one embodiment of the present invention.

FIG. 7 is a photograph of a large-capacity incubator according to one embodiment of the present invention.

FIG. 8 is a photograph of a large-capacity incubator provided with a cell culture sheet assembly according to the comparative example of the present invention in which contact between adjacent cell culture sheets occurs.

FIG. 9 is a photograph of large-capacity incubators according to one embodiment of the present invention, in which the left large-capacity incubator is in a state of being provided with a cell culture sheet and the right large-capacity incubator is in a state of having no cell culture sheet.

MODES OF THE INVENTION

Hereinafter, embodiments of the present invention will be described in detail with reference to the accompanying drawings such that a person with ordinary skill in the art to which the present invention pertains can easily carry out the present invention. The present invention can be realized in various forms, and is not limited to the examples described herein. In order to clearly describe the present invention in the drawings, parts not related to the description are omitted, and the same reference numerals are added to the same or similar constituent elements throughout the specification.

When described with reference to FIG. 1, in a cell culture sheet assembly 100 according to one embodiment of the present invention, a plurality of cell culture sheets 11, 12, and 13 are configured to be spaced apart at predetermined intervals in a direction perpendicular to the main surface. A spacer 20 between the adjacent cell culture sheets 11, 12, and 13 for maintaining the interval and a support 30 for fixing the plurality of cell culture sheets 11, 12, and 13 may be further included.

The cell culture sheets 11, 12, and 13 are a scaffold which has the upper surface and lower surface of each sheet as a main surface and allows cells to settle on the main surface and proliferate, and a fiber web, a film or a typical cell culture scaffold to which the fiber web and the film are bonded can be used without limitation.

However, to be suitable for a large-capacity culture method of cultivating cells in a state where large-area cell culture sheets each having a sheet area of 100 $cm^2$ or more are spaced apart in tiers at predetermined intervals or a large-capacity incubator used for the large-capacity culture method, the cell culture sheet according to one embodiment of the present invention is implemented so as to have a predetermined bending depth while having the sheet area of 100 $cm^2$ or more.

The reason why the cell culture sheet for a large-capacity incubator should have a predetermined bending depth will be described first with reference to FIG. 2.

As illustrated in FIG. 2, in a cell culture sheet assembly 100' having a plurality of cell culture sheets 1 and 2 disposed to be spaced apart at a predetermined interval, the cell culture sheets 1 and 2 may have sagging occurring in the central portion by their own weight, and even when the areas of the cell culture sheets 1 and 2 are increased or identical to each other, the sagging may be even worse when any one of the width and the length is larger. In addition, in order to increase the number of cell culture sheets 1 and 2 stacked in a limited volume, the cell culture sheet should be implemented so as to have a small thickness, but even in such a case, the sagging may become even worse. Furthermore, cells may be cultivated in a state where the cell culture sheet assembly 100' is impregnated with a cell culture fluid, and when the cell culture sheets 1 and 2 are wetted with the cell culture fluid, the weight becomes heavy, so that a sagging phenomenon due to their own weight may become even worse.

When the sagging of the cell culture sheets 1 and 2 occurs as in FIG. 2, contact may occur between an upper cell culture sheet 1 and a lower cell culture sheet 2, and a region A of the cell culture sheets 1 and 2 where contact occurs becomes a dead space, such that due to difficulties in cultivating cells in the corresponding portion, a decrease in volume capable of cultivating cells is induced and the cell culture fluid cannot also smoothly pass, thereby remarkably decreasing cell culture efficiency. Furthermore, when the cell culture fluid is introduced and flows into a space between the upper cell culture sheet 1 and the lower cell culture sheet 2 at a predetermined flow rate, a difference in flow rates occurs when passing through the space between the adjacent cell culture sheets 1 and 2 where sagging occurs, and as the existing cell culture fluid is not replaced while a cell culture fluid is smoothly supplied to a portion through which the cell culture fluid passes at a slow flow rate for this reason, cell culture efficiency may deteriorate. Further, in contrast, in a portion to which the cell culture fluid passes at a fast rate, the shaking of the cell culture sheet may occur due to the fast flow rate, and in this case, it may be difficult for cells to be cultivated by being stably attached to the cell culture sheet, so a decrease in cell culture efficiency may be induced.

Therefore, in a large-capacity culture method of cultivating cells in a state where a plurality of large-area cell culture sheets each having a sheet area of 100 $cm^2$ or more are spaced apart in tiers at predetermined intervals or a large-capacity incubator implemented in such a disposition form, all typical cell culture sheets cannot be used, and when a plurality of large-area cell culture sheets are disposed to be spaced apart in tiers at predetermined intervals, it is required to adopt a cell culture sheet in which properties are realized such that it is possible to prevent the occurrence of a dead space and there is little shaking despite the fast flow rate of the cell culture fluid.

Meanwhile, it can be considered to provide a separate supporting member (for example, a spacer to be described below, and the like) which supports a portion where sagging occurs in order to prevent the sagging of the cell culture sheet, and as a cell culture sheet region supported by the supporting member becomes a dead space where cells cannot be cultivated, the method may not be appropriate as a method for cultivating as many cells as possible in a limited volume.

Thus, as the cell culture sheet assembly according to the present invention is formed of a cell culture sheet so as to satisfy a predetermined bending depth despite having a large sheet area of 100 $cm^2$ or more, preferably 200 $cm^2$ or more, and more preferably 400 $cm^2$ or more, sagging due to its own weight, and the like is prevented even when used in a large-capacity incubator, and shaking due to the flow of a culture fluid supplied to the inside of the large-capacity incubator is minimized, so that cells can be stably cultivated.

In this case, when the bending depth is described with reference to FIG. 3, a bending depth d indicates the degree of bending when in a state where a first portion l, which is a region from any one corner perpendicular to a longitudinal direction of a cell culture sheet 10 cut into a length and width of 18 cm and 3 cm, respectively to a first line which is 12.5 cm away from the corner in a longitudinal direction, is pressed with a zig having a weight of 500 g and fixed to the upper surface of a table T, the other 5.5 cm portion in the longitudinal direction is bent by its own weight, and the bending depth d is measured as a vertical distance from the upper surface of the first part l to the upper corner of the tip of the remaining bent portion.

The cell culture sheet 11, 12, and 13 provided in the cell culture sheet assembly 100 according to the present invention may have a bending depth d of 0.5 cm or less, preferably 0.35 cm or less. When the bending depth d exceeds 0.5 cm, sagging occurs when a plurality of sheets having a large area of 100 $cm^2$ or more are disposed to be spaced apart at predetermined intervals, so that a dead space where contact occurs between adjacent cell culture sheets may be generated, and when a culture fluid flows at a predetermined flow rate between adjacent cell culture sheets, the shaking of the cell culture is severe, so it may be difficult to stably cultivate cells. However, even when the cell culture sheet has a bending depth of 0.5 cm or less, the bending depth may be 0.01 cm or more, and when the cell culture sheet has a bending depth of less than 0.01 cm, the thickness of the cell culture sheet becomes excessively large, such that there may be a risk that the number of cell culture sheets provided in a limited volume is decreased or a process of punching the sheet into a predetermined shape or size is not easily performed. In addition, in the case of a thick film-type cell culture sheet, the film is mass-produced and sold in a roll shape due to the film manufacturing process, and in the case of the film described above, when the film is punched so as to have an area of particularly 100 $cm^2$ or more, a curvature of a certain number or more is continuously maintained without maintaining a flat state, so the cell culture sheet may not be suitable as a cell culture sheet provided in the cell culture sheet assembly.

Meanwhile, to prevent contact between adjacent sheets due to the excessive sagging of the cell culture sheet, it is possible to tolerate the sagging of the cell culture sheet and increase the distance between sheets, and since the aforementioned method decreases the number of cell culture sheets which may be disposed to be spaced apart in a limited volume (that is, height), it should be noted that the method goes against the present invention intended to implement a cell culture sheet suitable for a large-capacity culture incubator, and is not considered by the present invention.

The cell culture sheets 11, 12, and 13 are not limited as long as they are formed of a material used as a typical cell culture scaffold. As an example, the cell culture sheets 11, 12, and 13 may be formed of any one or more non-biodegradable components selected from the group consisting of polystyrene (PS), polyester, polyethersulfone (PES), polyacrylonitrile (PAN), polydimethylsiloxane (PDMS), polyamide, a polyalkylene, poly(alkylene oxide), poly (amino acids), poly(allylamines, polyphosphazene, polyurethane, and a polyethylene oxide-polypropylene oxide block copolymer, any one or more biodegradable components selected from the group consisting of polycaprolactone, polydioxanone, polyglycolic acid, poly(L-lactide)(PLLA), poly(DL-lactide-co-glycolide)(PLGA), polylactic acid), and polyvinyl alcohol, a mixture thereof, or a copolymer thereof. Preferably, the cell culture sheets 11, 12, and 13 may include any one or more components selected from the group consisting of polystyrene (PS), polyester, polyethersulfone (PES), polyvinylidene fluoride (PVDF), polydimethylsiloxane (PDMS), polyamide, polyimide, polyethylene, and polypropylene.

Furthermore, the cell culture sheets 11, 12, and 13 may be implemented by including any one or more of a fiber web and a film. Specifically, the cell culture sheets 11, 12, and 13 may be a single fiber web or film alone, or a laminate including a plurality of fiber webs or films. The cell culture sheets 11, 12, and 13 may also be a laminate in which one or more fiber webs and one or more films are bonded and integrated. In this case, when the fiber web and the film are bonded, the fiber web and the film may be bonded through an adhesive such as a silicone material, or may be bonded by partial melting of the film or the fiber web without an adhesive. According to one embodiment, the cell culture sheet may be a laminate in which a fiber web and a film supporting the fiber web are integrated. In this case, the cell culture sheet is advantageous for effectively settling and proliferating cells using the morphology of the surface of the fiber web, and may be advantageous for the three-dimensional growth of cells because the cells can also be proliferated in a space formed through the pores inside the fiber web. Further, the film integrated on one surface has a benefit in that, after cells settle on the fiber web, it can be more advantageous for preventing the cells from passing through the inside of the fiber web and being detached downward due to its own weight and simultaneously achieving the bending depth according to the present invention. Furthermore, as the fiber web and the film are stacked, handleability is improved, so that the cell culture sheet can be easily mounted in the incubator. In addition, when the fiber web is coated with a physiologically active component to be described below, for example, a motif which is a peptide, the coating surface can implement a topology that is more helpful for cell attachment, regeneration and proliferation by the morphology of the fiber web, and thus may be more advantageous for cell proliferation. Meanwhile, even in the case of the fiber web, when the fiber diameter is large, the density of the fiber web is small, and the effect of the topology described above may be insignificant. Further, a cell culture sheet provided with a fiber web may be more advantageous for cell recovery compared to the case of the film alone, and in particular, the larger the area of the cell culture sheet is, the better the cell recovery property may be.

The fiber web may be implemented in a web shape by a known method such as spunbond or melt blown, or may be implemented by electrospinning. In addition, the fiber web is formed of fibers having an average diameter of 10 nm to 1.5 µm, and may have a basis weight of 1 to 20 g/m$^2$. When the average diameter of the fibers is less than 10 nm, mechanical strength deteriorates and it may be difficult to produce a fiber web. When the average diameter of the fibers is more than 1.5 µm, there is a risk that the density (basis weight) of the fiber web becomes low, and the surface of the fiber web may be formed as if it were partially melted during thermocompression bonding. Furthermore, it is difficult for the fiber web morphology to implement a topology that is advantageous for cell culture, such that there is a risk that cell culture efficiency is decreased. Further, when the basis weight is less than 1 g/m$^2$, there is a risk that handleability is not easy when the fiber web is produced, and when the basis weight is more than 20 g/m$^2$, the fiber web may be melted by a pressing roll, and when the fiber web is laminated with a film to implement a cell culture sheet, it may be difficult for the fiber web to be attached to the film. In addition, when fiber diameter and fiber web basis weight conditions are not satisfied, it may be difficult to implement a surface morphology suitable for cell culture, and it may be difficult to achieve a level of cell culture efficiency and the like targeted by the present invention.

Furthermore, the film may be implemented as a film by a known method, and for example, may be formed such that a component, which forms a film, is melted to be extruded through a die, or a component, which forms a film, is melted, and then applied on a substrate to have a predetermined thickness by a typical coating method. Further, a cell culture sheet, which is a film, may be a sheet whose surface is modified by plasma treatment and the like to improve hydrophilicity, and a surface modification method for improving hydrophilicity may be performed by a known method, and thus is not particularly limited by the present invention. In addition, after cells are loaded, the cell culture sheet, which is a film, may have fine curves, grooves, and the like formed on the surface so as to have a predetermined surface roughness in order to improve the adhesive force between the film surface and the cells.

The cell culture sheets 11, 12, and 13 may have a thickness of preferably 200 to 800 µm, more preferably 250 to 700 µm, and even more preferably 300 to 520 µm. When the thickness is less than 200 µm, the thickness is so small that it may be difficult to satisfy the bending depth according to the present invention due to the thinness. In particular, when the cell culture sheet is implemented with a fiber web alone, it may be difficult to satisfy the bending depth even by adjusting the diameter/basis weight of the fibers, and the like. Further, there is a risk that shape deformation such as distortion and warping of the cell culture sheet may be induced during the high temperature and high pressure treatment performed for a sterilization process and contact between the cell culture sheets without their own weight may occur due to the shape deformation. Furthermore, there is a risk that, when the cell culture sheet is implemented with a large area of 100 cm$^2$ or more, contact between adjacent cell culture sheets may occur and the contact area may increase, particularly, because the central portion sags excessively. Furthermore, the cell culture sheet may be excessively shaken by the cell culture fluid supplied at a constant flow rate, which may make it difficult for cells to be stably attached and proliferated. Further, when the thickness is more than 800 μm, the number of cell culture sheets stacked in a limited volume may decrease. In addition, there is an advantage in that when the cell culture sheet is in the form of a fiber web shape, the cell culture fluid flows into the fiber web and then flows vertically and horizontally inside the fiber web, so that the cells can be more smoothly brought into contact with a fresh cell culture fluid, but there is a risk that when the thickness is excessively thick, the flow and exchange of cell culture fluid which may occur inside the fiber web may not be smooth, and thus the proliferation of cells deteriorates, or the cells that proliferate inside the fiber web may die. Furthermore, when the thickness is large, the weight is likely to be heavier, and in this case, there is a risk that the increase in weight due to the wetting of the cell culture fluid may accelerate the occurrence of sagging, and when the cell culture sheet includes a fiber web, the sagging due to the wetting of the cell culture fluid may be worse. In addition, there is a risk that, when the cell culture sheet is formed of a thick film or includes a thick film, punching is not easily performed, and when the interval between cell culture sheets is disposed to be narrow because the cell culture sheet has a permanent curvature due to the characteristics of a film which is mass-produced and sold, the contact between sheets and a dead space may occur due to the curvature.

Meanwhile, it is possible to sterilize the cell culture sheet under high temperature and high pressure conditions, and the cell culture sheet may have a thickness of preferably 300 to 520 μm to prevent the above-described various problems from occurring despite the sterilization under these conditions.

Furthermore, when the cell culture sheet 11, 12, and 13 are a laminate in which the fiber web and the film are integrated, it is preferred that the fiber web has a thickness of 1 to 10 μm, which may express more improved cell proliferation effects, and may be more advantageous, particularly, for the proliferation of stem cells. More preferably, in the fiber web, the provided fibers may be implemented to have an average diameter of 200 to 300 nm, and the fiber web may be implemented to have a basis weight of 2.5 to 6.5 g/m$^2$, more preferably 3 to 5 g/m$^2$. Further, in this case, the fiber web may have a thickness of 4 to 6 μm. In addition, the fiber web may be implemented to have an air permeability of 1 to 4 cfm. Since the surface morphology of a cell culture sheet including a fiber web implemented to have these characteristics may be very suitable for human induced pluripotent stem cells (hiPSCs), human cardiac stem cells (hCSCs), mesenchymal stem cells (MSCs), and mouse embryonic stem cells (mESCs), very excellent culture efficiency may be expressed for these cells, and the cultured cells may be cultivated so as to have a diameter smaller than that at the time of seeding, which is advantageous for cultivating younger and better cells. As an example, the hCSCs may have a diameter of 24 to 25 μm at the time of seeding, but cells proliferated after cultivation may have a diameter of 16 to 18 μm.

As another example, in the fiber web, the provided fibers may be implemented to have an average diameter of 500 to 600 nm, and the fiber web may be implemented to have a basis weight of 3 to 12 g/m$^2$, more preferably 3 to 10 g/m$^2$, and for example, 4.0 to 5.5 g/m$^2$. Furthermore, in this case, the fiber web may have a thickness of 3 to 6 μm, more preferably 5 to 6 μm. Further, the fiber web may be implemented to have an air permeability of 4.5 to 8.0 cfm. The surface morphology of a cell culture sheet including a fiber web implemented to have these characteristics may also be suitable for human induced pluripotent stem cells (hiPSCs), human cardiac stem cells (hCSCs), mesenchymal stem cells (MSCs), and mouse embryonic stem cells (mESCs), but may express better culture efficiency for mesenchymal stem cells which produce osteoblasts which differentiate into bone cells. In addition, the cultivated cells may be cultivated so as to have a diameter smaller than that at the time of seeding, which is advantageous for cultivating younger and better cells.

Furthermore, the cell culture sheets 11, 12, and 13 may have an area of 100 cm$^2$ or more, and a length and width of, for example, 11 cm×11 cm, or 18 cm×13 cm.

Meanwhile, there is no limitation in a method of implementing a single cell culture sheet, which is a fiber web, a film, or a laminate to which the fiber web and the film are bonded so as to have the above-described bending depth. As an example of adjusting a desired predetermined bending depth, the thickness may be adjusted within the preferred range, the number of stacked layers may be adjusted, the material may be changed, the diameter and/or basis weight of forming a web in the case of a fiber web may be adjusted, and since mechanical strength may be achieved by stacking excellent heterogeneous fiber webs or films, specific descriptions on this will be omitted in the present invention.

However, it is difficult to see that the occurrence of sagging due to the own weight of the large-area cell culture sheet is greatly affected by the thickness of the cell culture sheet as a single factor and rather, may be much more affected by bending characteristics, creep, thermal deformation temperature, coefficient of thermal expansion, and difference in contraction and expansion rate in the TD and MD directions of a punched cell culture sheet, and the directionality (for example, whether the MD direction is a longitudinal direction or width direction of the punched sheet, or a direction other than the longitudinal and width directions, and the like). Accordingly, it is possible to implement the bending depth of the present invention by the combined adjustment of these factors.

Further, the cell culture sheets 11, 12, and 13 may have a bending depth of 0.5 cm or less measured after being allowed to stand at 121° C. and 1.15 atm for 1 hour. The cell culture sheet may be subjected to a sterilization process under high temperature and high pressure conditions before cells are loaded, and as the cell culture sheet is maintained in a state of being immersed in the cell culture fluid during the cell culture process, a shape maintenance ability which prevents sagging is required even under high temperature and high humidity conditions. Accordingly, even when a cell culture sheet satisfying a bending depth of 0.5 cm or less measured after being allowed to stand at 121° C. and 1.15 atm for 1 hour is subjected to a sterilization process at high temperature, and then the cells are continuously cultivated for a long time while being immersed in the cell culture fluid, it may be advantageous for preventing the occurrence of a dead space and more stably cultivating a large number of cells. In this case, as an example of a cell culture sheet satisfying these conditions, a film made of a material such as a highly heat-resistant polyester, polyimide, or polycarbonate may be used alone, or a form in which such a film of such a material and a fiber web are stacked may be used, and in the case of a polystyrene film, there is a risk that shape deformation may be caused during processing under high temperature and high pressure sterilization conditions.

In addition, the cell culture sheets 11, 12, and 13 may have a predetermined curvature in any one direction of the width direction or the longitudinal direction. This is because when a cell culture sheet formed with a curvature is stacked such that the convex portion of the cell culture sheet is in a direction opposite to the direction of its own weight, the sagging of the central portion due to its own weight may be offset, and even in this case, the cell culture sheet may have a radius of curvature of 0.1 to 0.5 mm, but when the radius of curvature is less than 0.1 mm, the effect of offsetting the influence by the own weight may be insignificant, and when the radius of curvature is more than 0.5 mm, contact between adjacent cell culture sheets may occur due to the excessive curvature.

Meanwhile, the surfaces of the cell culture sheets 11, 12, and 13 may be provided with a physiologically active component having a function of inducing or promoting any one or more of cell attachment, migration, proliferation and differentiation.

The physiologically active component may include any one or more of any one or more compounds selected from the group consisting of monoamines, amino acids, peptides, saccharides, lipids, proteins, glucoproteins, glucolipids, proteoglycans, mucopolysaccharides and nucleic acids, and cells. The physiologically active materials may be, specifically, a material present in an extracellular matrix, or a material that is artificially produced to be identical or similar to the material.

Furthermore, the physiologically active component may include a motif. The motif may be a natural peptide or a recombinant peptide including a predetermined amino acid sequence provided in any one or more selected from the group consisting of a protein, a glycoprotein, and a proteoglycan included in a growth factor or an extracellular matrix. Specifically, the motif may include a predetermined amino acid sequence included in any one or more growth factors (GFs) selected from the group consisting of adrenomedullin, angiopoietin, a bone morphogenetic protein (BMP), brain-derived neurotrophic factor (BDNF), an epidermal growth factor (EGF), erythropoietin, a fibroblast growth factor, a glial cell line-derived neurotrophic factor (GDNF), a granulocyte colony-stimulating factor (G-CSF), a granulocyte macrophage colony-stimulating factor (GM-CSF), growth differentiation factor-9 (GDF9), a hepatocyte growth factor (HGF), a hepatoma-derived growth factor (HDGF), an insulin-like growth factor (IGF), a keratinocyte growth factor (KGF), a migration-stimulating factor (MSF), myostatin (GDF-8), a nerve growth factor (NGF), a platelet-derived growth factor (PDGF), thrombopoietin (TPO), a T-cell growth factor (TCGF), neuropilin, transforming growth factor-alpha (TGF-α), transforming growth factor-beta (TGF-β), tumor necrosis factor-alpha (TNF-α), a vascular endothelial growth factor (VEGF), IL-1, IL-2, IL-3, IL-4, IL-5, IL-6, and IL-7. Alternatively, the motif may include a predetermined amino acid sequence included in any one or more extracellular matrix components selected from the group consisting of hyaluronic acid, heparin sulfate, chondroitin sulfate, dermatan sulfate, keratan sulfate, alginate, fibrin, fibrinogen, collagen, elastin, fibronectin, vitronectin, cadherin, and laminin.

Further, the motif may also include both a predetermined amino acid sequence included in a growth factor and a predetermined amino acid sequence included in the extracellular matrix component. More preferably, the motif may include one or more selected from the group consisting of proteins including SEQ ID NOS: 8 to 28 and a protein in which at least two of these proteins are fused, but is not limited thereto.

Meanwhile, the cell culture sheets 11, 12, and 13 may further include an adhesive component. The adhesive component may perform a function of preventing cells loaded on a culture solution from floating by fixing cultivated cells on a cell culture sheet at the initial stage and/or a function of preventing a physiologically active component from being detached from a cell culture sheet during the cell culture process by fixing the physiologically active component rather than an adhesive component on the cell culture sheet.

The adhesive component may include a known mussel protein or a specific domain or motif of the mussel protein to enhance the adhesion of cells. As the adhesive component, an adhesive component that is typically biocompatible and does not cause cytotoxicity can be used without limitation, but the adhesive component may preferably include one or more selected from the group consisting of proteins produced by repeating the amino acid sequences of SEQ ID NOS: 1 to 7 1 to 20 times and proteins in which at least two of these proteins are fused, and through this, there are advantages in that cytotoxicity significantly deteriorates, the adhesive strength of a physiologically active component is excellent, and simultaneously it is possible to prevent a physiologically active component generated as an adhesive component is dissolved in a culture solution from being detached or cells from being isolated.

In addition, when the physiologically active component is a motif, the motif may be covalently bonded to an adhesive component and integrally implemented. As an example, when the adhesive component is a protein, the motif may be covalently bonded directly to the N-terminal and/or C-terminal of a polypeptide, or may be covalently bonded by interposing a heterologous peptide or polypeptide, and in this case, a physiologically active component may be more firmly attached to a cell culture sheet, and the detachment of the physiologically active component during cell culture may be minimized.

Furthermore, the above-described physiologically active component may be provided on the surfaces of cell culture sheets 11, 12, and 13 by a known method. As an example, the physiologically active component may be provided on the surface of a fiber web or film through a coating process. When the surface of the fiber web is coated with the physiologically active component, the outer surfaces of fibers constituting the fiber web are coated while maintaining the porous structure of the fiber web and/or the surface side of the fiber web may also be intensively coated while partially blocking the porous structure on the surface side of the fiber web. Alternatively, the physiologically active substance may be mixed with a polymer compound that forms a fiber web or a film to be provided from a step of preparing a crude liquid for the production of the fiber web or the film. In this case, there is an advantage in that a physiologically active material may be easily provided without a separate coating process or a separate adhesive component for fixing a physiologically active material on the outer surface of the produced fiber web or film.

Next, a spacer 20 disposed between adjacent cell culture sheets 11, 12, and 13 will be described. The spacer 20 serves to maintain a predetermined interval between adjacent cell culture sheets when a plurality of cell culture sheets 11, 12, and 13 are stacked in tiers. A material that is not dissolved in a cell culture fluid can be used without limitation when the spacer 20 has a shape that does not obstruct the flow of the cell culture fluid.

In this case, the thickness of the spacer 20 may be a distance between cell adjacently disposed culture sheets.

Further, referring to FIGS. 4 and 5, the shape of the spacer 20 as in FIG. 4 may be a shape of an O-ring, or a spacer 20' as in FIG. 5 may have a shape that has a predetermined width and is formed long in one direction, but the shape is not limited thereto.

In addition, the support 30 serves to fix the above-described cell culture sheets 11, 12, and 13 and the spacer 20. The support 30 is formed of a material which is not dissolved in a cell culture fluid, and the diameter thereof may be equal to or smaller than that of a hole provided in the cell culture sheets 11, 12, and 13 and the spacer 20.

When described by referring to FIGS. 4 and 5, in the cell culture sheet assembly 100 or 100", the cell culture sheets 11, 12, and 13 may be provided with a first hole (H1) passing therethrough at predetermined intervals along the edge of each cell culture sheet, the spacer 20 or 20' may be provided with a second hole H2 or H'2, the spacer 20 or 20' is disposed between cell culture sheets 11, 12, and 13 such that the second hole H2 or H2 corresponds to the first hole H1 of the adjacently disposed cell culture sheets 11, 12, and 13, and the support 30 may be inserted so as to pass through the first hole H1 and the second hole H2 or H'2 parallel to a stacking direction of the cell culture sheets 11, 12 and 13 to fix the cell culture sheets 11, 12, and 13 and the spacer 20 or 20'.

The diameter of the second hole H2 provided in the spacer 20 may be the same as the diameter of the first hole H1, but is not limited thereto. Furthermore, a distance between the adjacent first holes (H1) may be 5 cm, more preferably 2.5 cm, and even more preferably 1 cm or less, and through this, there is an advantage in that the sagging of the cell culture sheet may be further prevented structurally.

The cell culture sheet assembly illustrated in FIG. 1 may be accommodated inside a housing to implement a large-capacity incubator. In this case, since the inside of the housing may be provided with a groove in which the end of the support 30 is accommodated, the cell culture sheet assembly 100 to be accommodated may be fixed inside the housing. Alternatively, the housing may be provided with a hole through which the end of the support 30 passes, and after the support 30 is inserted into the hole, the end of the support 30 may also be fixed inside the housing by a method of being fastened by a separate fastening member such as a nut from outside the housing.

Meanwhile, unlike FIGS. 1 and 4, a cell culture sheet assembly 200 according to one embodiment of the present invention may be formed by a method in which a plurality of cell culture sheets 14, 15, and 16 are insertion-fitted into slits formed on the inner surface of a housing 40 of a large-capacity incubator 1000 as illustrated in FIG. 6 in such a manner that predetermined intervals are formed. In this case, the housing 40 may have a structure in which all the remaining surfaces are closed except for one side wall into which the cell culture sheets 14, 15, and 16 are inserted. In this case, the cell culture sheet 14, 15, and 16 may form a cell culture sheet assembly 200 in which a plurality of cell culture sheets are spaced apart by a predetermined vertical distance without a separate member which spaces cell culture sheets apart such as a spacer.

The cell culture sheet assembly according to another embodiment of the present invention may be implemented by further including a guide member having a modified structure of a housing 40 in FIG. 6 along with a plurality of cell culture sheets. The guide member may be implemented such that the housing 40 in FIG. 6 has a structure in which the remaining side wall portions except for both side walls where slits 41 are formed, and the upper and lower portions are open. In this case, the cell culture sheet assembly in which a plurality of cell culture sheets are mounted into the slits of the guide member becomes one unitary unit such as a cartridge, and a plurality of unitary units may be accommodated inside the housing to form a large-capacity incubator.

The above-described cell culture sheet assemblies 100, 100", and 200 may be provided with 10 to 100 cell culture sheets, but is not limited thereto because the number may be appropriately changed depending on the capacity of the large-capacity incubator.

In the cell culture sheet according to the present invention described above, a plurality of the sheets may be stacked to be spaced apart at predetermined intervals between the sheets to implement a large-capacity incubator.

In this case, the interval between sheets of the cell culture sheet may be 0.1 to 50 mm, more preferably 0.1 to 20 mm, even more preferably 0.5 to 20 mm, and even much more preferably 0.5 to 12 mm. When the interval between the cell culture sheets is more than 100 mm, the number of the cell culture sheets to be provided in a limited space may be reduced. When the interval is less than 0.1 mm, it may be difficult for the cell culture fluid to pass through a separation space between the cell culture sheets formed by the predetermined intervals, and as a result, there is a risk that cell culture efficiency may be reduced. Further, there is a risk that even a cell culture sheet having a bending depth according to the present invention may generate a dead space during the occurrence of sagging due to its own weight after being wetted with the cell culture fluid.

Meanwhile, the above-described housing, which is one component of the large-capacity incubator, may be provided with an empty space therein such that the cell culture sheet assembly can be accommodated. In addition, the housing may further include a cell culture fluid inlet and outlet such that the cell culture fluid can flow into the housing and flow out to the outside for replacement of the cell culture fluid. In this case, the inlet and outlet may have a diameter of, for example, 0.5 to 5$\phi$ or 1 to 3$\phi$. Furthermore, the flow rate of the cell culture fluid flowing in through the inlet may be 80 ml/min or less, more preferably 20 to 50 ml/min, which is advantageous for minimizing the shaking of the cell culture sheet by the flow of the cell culture fluid formed inside the housing.

Further, the present invention may implement a cell culture system using the large-capacity incubator. The large-capacity cell culture system may be implemented by providing a large-capacity incubator, a medium supply device for supplying a medium required during cell culture on one side of the large-capacity incubator, and a pump for circulating the medium.

As the medium supply device and the pump, it is possible to appropriately adopt and change the configuration of those typically used for cultivating cells in a large volume in the art, and a specific description thereof will be omitted. Alternatively, for the large-capacity cell culture system including the specific structure of the large-capacity incubator, the medium supply device, and the pump, Patent Application No. 10-2018-0140008 by the applicant of the present invention is referenced, and when the cell culture sheet according to the present invention is adopted for the large-capacity cell culture system disclosed in the patent document, it may be advantageous for cultivating a significantly larger amount of cells.

In addition, cells cultivated on the above-described cell culture sheet assembly according to one embodiment of the present invention, specifically a cell culture sheet constituting the cell culture sheet assembly may be implemented as a tissue engineering transplant along with a cell culture sheet assembly or each cell culture sheet separated from the cell culture sheet assembly. In this case, as the cell culture sheet, a cell culture sheet implemented by a biodegradable component may be used, but in this case, the cell culture sheet can be transplanted into the human body or the like as it is. In addition, the cells may include any one or more stem cells selected from the group consisting of omnipotent stem cells, pluripotent stem cells, multipotent stem cells, oligopotent stem cells and single stem cells, and one or more of differentiated cells selected from the group consisting of blood marrow cells, hepatocytes, fibrous cells, epithelial cells, mesothelial cells, endothelial cells, muscle cells, nerve cells, immune cells, adipocytes, chondrocytes, osteocytes, blood cells and skin cells.

The following Table 1 shows amino acid sequences for the above-described physiologically active components.

TABLE 1

| SEQ ID NO | Amino acid sequence |
|---|---|
| 1 | Met Ala Lys Pro Ser Tyr Pro Pro Thr Tyr Lys Ala Lys Pro Ser TyrPro Pro Thr Tyr Lys Ala Lys Pro Ser Tyr Pro Pro Thr Tyr Lys AlaLys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 2 | Met Ala Lys Pro Ser Tyr Pro Pro Thr Tyr Lys Ala Lys Pro Ser TyrPro Pro Thr Tyr Lys Ala Lys Pro Ser Tyr Pro Pro Thr Tyr Lys AlaLys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Gly Arg Gly Asp Ser Pro |
| 3 | Met Ala Lys Pro Ser Tyr Pro Pro Thr Tyr Lys Ala Lys Pro Ser TyrPro Pro Thr Tyr Lys Ala Lys Pro Ser Tyr Pro Pro Thr Tyr Lys AlaLys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Pro Trp Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr Gly Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Leu |
| 4 | Ala Asp Tyr Tyr Gly Pro Lys Tyr Gly Pro Pro Arg Arg Tyr Gly GlyGly Asn Tyr Asn Arg Tyr Gly Arg Arg Tyr Gly Gly Tyr Lys Gly TrpAsn Asn Gly Trp Lys Arg Gly Arg Trp Gly Arg Lys Tyr Tyr |
| 5 | Ser Ser Glu Glu Tyr Lys Gly Gly Tyr Tyr Pro Gly Asn Thr Tyr HisTyr His Ser Gly Gly Ser Tyr His Gly Ser Gly Tyr His Gly Gly TyrLys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser |
| 6 | Ala Lys Pro Ser Tyr Pro Pro Thr Tyr Lys |
| 7 | Ala Lys Pro Ser Tyr Pro Pro Thr Tyr Lys Ala Lys Pro Ser Tyr ProPro Thr Tyr Lys Ala Lys Pro Ser Tyr Pro Pro Thr Tyr Lys Ala LysPro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 8 | Arg Gly Asp |
| 9 | Arg Gly Asp Ser |
| 10 | Arg Gly Asp Cys |
| 11 | Arg Gly Asp Val |

TABLE 1-continued

| SEQ ID NO | Amino acid sequence |
|---|---|
| 12 | Arg Gly Asp Ser Pro Ala Ser Ser Lys Pro |
| 13 | Gly Arg Gly Asp Ser |
| 14 | Gly Arg Gly Asp Thr Pro |
| 15 | Gly Arg Gly Asp Ser Pro |
| 16 | Gly Arg Gly Asp Ser Pro Cys |
| 17 | Tyr Arg Gly Asp Ser |
| 18 | Ser Pro Pro Arg Arg Ala Arg Val Thr |
| 19 | Trp Gln Pro Pro Arg Ala Arg Ile |
| 20 | Asn Arg Trp His Ser Ile Tyr Ile Thr Arg Phe Gly |
| 21 | Arg Lys Arg Leu Gln Val Gln Leu Ser Ile Arg Thr |
| 22 | Lys Ala Phe Asp Ile Thr Tyr Val Arg Leu Lys Phe |
| 23 | Ile Lys Val Ala Asn |
| 24 | Lys Lys Gln Arg Phe Arg His Arg Asn Arg Lys Gly Tyr Arg Ser Gln |
| 25 | Val Ala Glu Ile Asp Gly Ile Gly Leu |
| 26 | Pro His Ser Arg Asn Arg Gly Asp Ser Pro |
| 27 | Asn Arg Trp His Ser Ile Tyr Ile Thr Arg Phe Gly |
| 28 | Thr Trp Tyr Lys Ile Ala Phe Gln Arg Asn Arg Lys |

Example 1

A fiber web formed of PVDF fibers having an average diameter of 260 nm, and having a basis weight of 4.5 g/m$^2$, and a thickness of 5 μm was prepared. After the fiber web was laminated so as to be brought into contact with a surface of a polycarbonate (PC) film having a thickness of 450 μm and provided with the silicone-based adhesive on one surface thereof, a cell culture sheet as shown in the following Table 2 was manufactured as an integrated laminate type that was attached using a coating machine (digital-3500plus) at room temperature.

Examples 2 to 7

A cell culture sheet was manufactured in the same manner as in Example 1, but a cell culture sheet as shown in the following Table 2 was manufactured by changing the material for the cell culture sheet, the structural specifications, and the like as in the following Table 2.

Comparative Examples 1 to 2

A cell culture sheet was manufactured in the same manner as in Example 1, but a cell culture sheet as shown in the following Table 2 was manufactured by changing the material for the cell culture sheet, the structural specifications, and the like as in the following Table 2.

Experimental Example 1

After the manufactured cell culture sheet was punched into a length and width of 18 cm and 3 cm, respectively, in a state where a first portion l, which is a region from any one corner perpendicular to a longitudinal direction of a punched specimen to a first line which is 12.5 cm away from the corner in a longitudinal direction, is pressed with a zig having a weight of 500 g and fixed to the upper surface of a table T as illustrated in FIG. 3, how much the remaining 5.5 cm portion in the longitudinal direction was bent by its own weight was measured, and the bending depth is shown in the following Table 2. Specifically, a bending depth d was measured as a vertical distance from the upper surface of the first part l to the upper corner of the tip of the remaining part bent portion. In addition, in order to evaluate the bending depth under high temperature and high pressure conditions, the cell culture sheet was punched to the same size, and then allowed to stand at 121° C. and 1.15 atm for 1 hour, and then the bending depth was measured by the same method as described above.

Experimental Example 2

After the cell culture sheets according to Examples and Comparative Examples were punched into a length and width of 11 cm and 11 cm, respectively, the cell culture sheets were perforated so as to correspond to the inner support of the right large-capacity incubator housing in FIG. 9. Then, the prepared cell culture sheet was irradiated with γ-rays at an intensity of 5 kGy to sterilize the cell culture sheet. Then, a spacer having a thickness of 1 mm and perforated so as to correspond to the diameter of the support was allowed to pass over the inner support of the large-capacity incubator housing. Then, one cell culture sheet was mounted to the inside of the large-capacity incubator such that a perforated hole was passed over the support. Then, a cell culture sheet assembly formed by spacing a total of 30 cell culture sheets at a vertical distance of 1 mm apart was implemented by a method of again allowing a spacer having a thickness of 1 mm to pass over the support and again mounting one cell culture sheet. Then, after the large-capacity incubator housing was sealed from the outside air, a cell culture fluid in which cells to be seeded were mixed was introduced by a cell culture fluid inlet tube provided on one side, and the cells were cultivated under a temperature condition of 37° C. for 5 days. In this case, as the cell culture fluid in which cells to be seeded was mixed, a cell culture fluid, which was obtained by introducing fetal bovine serum (FBS) into a medium in which 500 ml of a KBS-3 basal medium (B1001) and 2 ml of KSB-3 supplements (S2901) were mixed so as to be 10% of the total medium weight and including penicillin/streptomycin so as to be 1/100 of the total medium volume such that the number of mesenchymal stem cells (MSCs) in the cell culture fluid was 4,000 ea/cm$^2$ per unit area of the cell culture sheet, was used. Furthermore, when the culture conditions are described in detail, 24 hours after the seeding of cells, the cells were cultivated for a total of 5 days by replacing the cell culture fluid once with the same culture fluid.

Then, the cells proliferated by cultivation were collected and the number of cells was counted. Specifically, after the medium was removed from the large-capacity incubator, cells cultivated by injecting a 0.15% trypsin-EDTA solution whose temperature was adjusted to 37° C. into the housing, and then allowing to stand for a predetermined time were isolated from the cell culture sheet and suspended, and then the same cell culture fluid was injected again in order to neutralize the trypsin component, and then collected. Then, after the cells were precipitated and the supernatant was removed from the collected solution using a centrifuge, an extracted cell solution was mixed with a trypan blue solution at a ratio of 1:1, the number of cells was counted from the mixed solution using a cell counter, and a cell proliferation recovery rate calculated as a ratio of the number of cells recovered after proliferation to the number of seeded cells is shown in the following Table 2.

Furthermore, after the cell culture sheets according to Examples and Comparative Examples were punched into a length and width of 25 cm and 25 cm, respectively, cells were proliferated in the same manner as in the above method, and then the cell proliferation recovery rate was calculated, and is shown in the following Table 2.

Meanwhile, the size range of cells recovered in Examples 1 and 6 derived using a cell counter in the solution including the recovered cells is shown in the following Table 3.

Further, compared to cells seeded before cultivation, whether cells proliferated and recovered through Example 1/Example 6 were characteristically altered was analyzed by FACS using CD markers (CD29, CD44, CD73, CD10, CD11b, CD34, and CD45), and the results are shown along with the following Table 3.

TABLE 2

| | | Example 1 | Example 2 | Example 3 | Example 4 | Example 5 | Example 6 | Example 7 | Comparative Example 1 | Comparative Example 2 |
|---|---|---|---|---|---|---|---|---|---|---|
| Fiber web | Fiber average diameter (nm) | 260 | 300 | 260 | 500 | 260 | None | 260 | 300 | 600 |
| | Basis weight (g/m$^2$) | 4.5 | 5.0 | 4.5 | 5.8 | 4.5 | None | 4.5 | 5.0 | 6.2 |
| | Thickness (μm) | 5 | 5 | 5 | 3 | 5 | None | 5 | 6 | 10 |
| Film | Material | PC | PC | PC | PC | PS | PC | PC | PC | PC |
| | Thickness (μm) | 500 | 200 | 300 | 250 | 500 | 700 | 700 | 150 | 200 |
| Total thickness (μm) of cell culture sheet | | 505 | 205 | 305 | 253 | 505 | 700 | 705 | 155 | 210 |
| Bending depth (cm) | | 0.20 | 0.47 | 0.35 | 0.42 | 0.22 | 0.10 | 0.10 | 0.55 | 0.51 |
| Bending depth (cm) after being allowed to stand at 121° C. and 1.15 atm for 1 hour | | 0.23 | 0.55 | 0.40 | 0.49 | Cannot be measured | 0.13 | 0.13 | 0.64 | 0.58 |
| (11 cm × 11 cm) cell proliferation recovery rate (fold) | | 37.6 | 26.3 | 33.8 | 27.0 | 37.8 | 31.5 | 36.6 | 15.1 | 18.9 |
| (25 cm × 25 cm) cell proliferation recovery rate (fold) | | 32.9 | 20.4 | 25.6 | 20.2 | 32.0 | 22.3 | 28.8 | 10.6 | 7.4 |

As can be confirmed from Table 2, it can be seen that the examples corresponding to the cell culture sheet having a bending depth of 0.5 cm or less have a better cell proliferation recovery rate than the comparative examples. Specifically examining the results of the examples, when Example 4 and Example 2 are compared, Example 4 may be advantageous for cell culture due to the smaller bending depth, but a slight difference in cell proliferation recovery rate is expected to be due to a difference in fiber web specifications, and it can be seen that in cultured mesenchymal stem cells (MSCs), the morphology of the fiber web used in Example 2 is more advantageous for cell culture than the morphology of the fiber web used in Example 4. In the case of Example 5, the material of the film used is polystyrene, and although the cell proliferation recovery rate is similar to that of Example 1 when sterilized using g-rays, when sterilized under high temperature and high pressure conditions, the bending depth could not be measured because the film portion of the cell culture sheet melted. Accordingly, it can be seen that the polycarbonate film used in Example 1 has an advantage over Example 5 in that restrictions on the sterilization method are alleviated.

Meanwhile, in the case of Example 6, it can be seen that cell culture efficiency is excellent when the film is used alone, but the cell culture efficiency is slightly lower than that of Example 8. Meanwhile, in Example 7, a sheet having a size of 25 cm×25 cm has a slightly larger decrease in cell proliferation recovery rate than a sheet having a size of 11 cm×11 cm, and as a result of recovery as cells are proliferated by forming a membrane on a film, this is due to the fact that the cells are not isolated and there are cells that have been agglomerated and recovered.

Further, when comparing Example 1 and Example 7, it can be confirmed that, Example 1 has a higher cell proliferation recovery rate when the area is increased to a size of 25 cm×25 cm, which is expected to be due to the cell culture sheet of Example 7 being more affected by the wetting of the cell culture fluid than in Example 1 in a state of being immersed in the cell culture fluid.

TABLE 3

|  | Example 1 | Example 6 |
|---|---|---|
| Average size (µm) of isolated cells | 20.5 | 15.3 |
| Presence of change in characteristics of cells | None | None |

As could be confirmed from Table 3, it was confirmed that the cells proliferated and recovered by the cell culture sheets of Examples 1 and 6 had no change in cell characteristics. However, the size of the cells proliferated and recovered on the cell culture sheet of Example 1 is slightly smaller than the size of the cells proliferated and recovered on the cell culture sheet of Example 6, and through this, it can be seen that the cultivated cells are very young and the cell condition is excellent. The small size of cells proliferated and recovered by the cell culture sheet according to Example 1 is due to the topology effect caused by the fiber web morphology and the fiber web characteristics compared to the film, and it can be seen that this effect can be achieved even better by the preferred fiber web described in the present invention.

Although one embodiment of the present invention has been described above, the spirit of the present invention is not limited to the embodiments presented in present specification, and a person skilled in the art who understands the spirit of the present invention can easily propose other embodiments by substitutions, changes, deletions, additions, and the like of the constituent elements, but it can be said that those embodiments also fall within the scope of the spirit of the present invention.

The invention claimed is:

1. A cell culture sheet assembly for an incubator, the cell culture sheet assembly comprising: a plurality of cell culture sheets, wherein the plurality of cell culture sheets are disposed to be spaced apart in a direction perpendicular to a main surface, wherein a vertical distance between adjacent cell culture sheets is 0.5 to 20 mm, wherein each of the cell culture sheets is a laminate of a fiber web and a polymer film on a surface of the fiber web, wherein the fiber web has a thickness of 1 to 10 μm, wherein each of the cell culture sheets has an area of 100 cm$^2$ or more and a thickness of 200 to 800 μm, and wherein each of the cell culture sheets has a bending depth of 0.01 to 0.5 cm to prevent sagging due to weight of a cell culture.

2. The cell culture sheet assembly of claim 1, wherein the fiber web and/or the polymer film comprises any one or more components selected from the group consisting of polystyrene (PS), polyester, polyethersulfone (PES), polyvinylidene fluoride (PVDF), polydimethylsiloxane (PDMS), polyamide, polyimide, polyethylene, and polypropylene.

3. The cell culture sheet assembly of claim 1, wherein each of the cell culture sheets comprises the fiber web, wherein the fiber web has a basis weight of 1 to 20 g/m$^2$, which is formed of fibers having an average diameter of 10 nm to 1.5 μm.

4. The cell culture sheet assembly of claim 1, wherein each of the cell culture sheets has the bending depth of 0.01 to 0.5 cm measured after being allowed to stand at 121° C. and 1.15 atm for 1 hour.

5. The cell culture sheet assembly of claim 1, wherein each of the cell culture sheets has a predetermined curvature in any one direction of a width direction or longitudinal direction, and has a radius of curvature of 0.1 to 0.5 mm.

6. The cell culture sheet assembly of claim 1, wherein the main surface of each of the cell culture sheets comprises a physiologically active component having a function of promoting any one or more of cell attachment, migration, proliferation and differentiation.

7. A large-capacity incubator comprising: a housing having an internal space; and the cell culture sheet assembly of claim 1 accommodated in the internal space.

8. The large-capacity incubator of claim 7, wherein the cell sheet assembly further comprises first holes passing through at predetermined intervals along an edge of each cell culture sheet, a spacer provided with a second hole and
  a support having a diameter corresponding to the first holes and the second hole, and
  the spacer is disposed between adjacent cell culture sheets such that the first hole and the seconds hole of the cell culture sheet correspond to each other, and the support is inserted so as to pass through the first hole and the second hole disposed to correspond to each other.

9. The large-capacity incubator of claim 7, wherein slits formed to be spaced apart at predetermined intervals are provided on both facing inner surfaces of the housing such that each cell culture sheet in the cell culture sheet assembly is inserted along an inner side surface of the housing and fixed.

* * * * *

SEQUENCE LISTING

```
<160> NUMBER OF SEQ ID NOS: 28

<210> SEQ ID NO 1
<211> LENGTH: 309
<212> TYPE: PRT
<213> ORGANISM: Artificial Sequence
<220> FEATURE:
<223> OTHER INFORMATION: adhesive component

<400> SEQUENCE: 1

Met Ala Lys Pro Ser Tyr Pro Pro Thr Tyr Ala Ala Lys Ala Lys Pro
1               5                   10                  15

Ser Tyr Pro Pro Thr Ala Tyr Ala Lys Ala Lys Pro Ser Tyr Pro Pro
            20                  25                  30

Ala Thr Tyr Ala Lys Ala Lys Pro Ser Tyr Pro Ala Pro Thr Tyr Ala
        35                  40                  45

Lys Ala Lys Pro Ser Tyr Ala Pro Pro Thr Tyr Ala Lys Ala Lys Pro
    50                  55                  60

Ser Ala Ala Ala Ala Ala Ala Ala Ala Ala Tyr Pro Pro Thr
65                  70                  75                  80

Tyr Ala Ala Ala Ala Ala Ala Ala Ala Ala Ala Lys Ser Ser
                85                  90                  95

Glu Ala Glu Tyr Lys Gly Gly Tyr Ala Tyr Pro Gly Ala Asn Thr Tyr
            100                 105                 110

His Tyr His Ser Ala Gly Gly Ala Ser Tyr His Gly Ser Gly Tyr His
        115                 120                 125

Ala Gly Ala Gly Tyr Lys Gly Lys Tyr Tyr Gly Lys Ala Ala Ala Ala
    130                 135                 140

Ala Ala Ala Ala Ala Ala Ala Ala Lys Lys Tyr Tyr Lys Tyr
145                 150                 155                 160

Lys Asn Ala Ala Ser Gly Lys Tyr Lys Tyr Leu Lys Lys Ala Ala Ala
                165                 170                 175
```

Ala Ala Ala Ala Ala Ala Ala Ala Ala Arg Lys Tyr His Arg
            180                 185                 190

Lys Gly Tyr Ala Lys Ala Tyr Tyr Gly Gly Ser Ser Ala Ala Lys
        195                 200                 205

Pro Ser Ala Tyr Pro Pro Thr Tyr Lys Ala Ala Ala Ala Ala Ala
    210                 215                 220

Ala Ala Ala Ala Ala Lys Pro Ser Ala Tyr Pro Pro Thr Tyr Ala Lys
225                 230                 235                 240

Ala Lys Pro Ser Ala Tyr Pro Pro Thr Ala Tyr Lys Ala Lys Pro Ser
                245                 250                 255

Ala Tyr Pro Pro Ala Thr Tyr Lys Ala Lys Pro Ser Ala Ala Ala
            260                 265                 270

Ala Ala Ala Ala Ala Ala Ala Tyr Pro Ala Pro Thr Tyr Lys Ala
        275                 280                 285

Lys Pro Ser Ala Tyr Ala Ala Ala Ala Ala Ala Ala Ala
        290                 295                 300

Pro Pro Thr Tyr Lys
305

<210> SEQ ID NO 2
<211> LENGTH: 202
<212> TYPE: PRT
<213> ORGANISM: Artificial Sequence
<220> FEATURE:
<223> OTHER INFORMATION: adhesive component

<400> SEQUENCE: 2

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Tyr Lys Tyr Lys Asn Ser Gly
            100                 105                 110

Lys Tyr Lys Tyr Leu Lys Lys Ala Arg Lys Tyr His Arg Lys Gly Tyr
        115                 120                 125

Lys Lys Tyr Tyr Gly Gly Ser Ser Ala Lys Pro Ser Tyr Pro Pro Thr
    130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys Gly Arg Gly Asp Ser Pro
        195                 200

<210> SEQ ID NO 3
<211> LENGTH: 172

```
<212> TYPE: PRT
<213> ORGANISM: Artificial Sequence
<220> FEATURE:
<223> OTHER INFORMATION: adhesive component

<400> SEQUENCE: 3

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Pro Trp Ala
    50                  55                  60

Asp Tyr Tyr Gly Pro Lys Tyr Gly Pro Pro Arg Arg Tyr Gly Gly
65                  70                  75                  80

Asn Tyr Asn Arg Tyr Gly Arg Arg Tyr Gly Gly Tyr Lys Gly Trp Asn
                85                  90                  95

Asn Gly Trp Lys Arg Gly Arg Trp Gly Arg Lys Tyr Tyr Gly Ser Ala
            100                 105                 110

Lys Pro Ser Tyr Pro Pro Thr Tyr Lys Ala Lys Pro Ser Tyr Pro Pro
        115                 120                 125

Thr Tyr Lys Ala Lys Pro Ser Tyr Pro Pro Thr Tyr Lys Ala Lys Pro
    130                 135                 140

Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170

<210> SEQ ID NO 4
<211> LENGTH: 46
<212> TYPE: PRT
<213> ORGANISM: Artificial Sequence
<220> FEATURE:
<223> OTHER INFORMATION: adhesive component

<400> SEQUENCE: 4

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 5
<211> LENGTH: 76
<212> TYPE: PRT
<213> ORGANISM: Artificial Sequence
<220> FEATURE:
<223> OTHER INFORMATION: adhesive component

<400> SEQUENCE: 5

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Lys
        35                  40                  45

Asn Ser Gly Lys Tyr Lys Tyr Leu Lys Lys Ala Arg Lys Tyr His Arg
```

```
                50                  55                  60
Lys Gly Tyr Lys Lys Tyr Tyr Gly Gly Gly Ser Ser
 65                  70                  75

<210> SEQ ID NO 6
<211> LENGTH: 10
<212> TYPE: PRT
<213> ORGANISM: Artificial Sequence
<220> FEATURE:
<223> OTHER INFORMATION: adhesive component

<400> SEQUENCE: 6

Ala Lys Pro Ser Tyr Pro Pro Thr Tyr Lys
 1               5                  10

<210> SEQ ID NO 7
<211> LENGTH: 60
<212> TYPE: PRT
<213> ORGANISM: Artificial Sequence
<220> FEATURE:
<223> OTHER INFORMATION: adhesive component

<400> SEQUENCE: 7

Ala Lys Pro Ser Tyr Pro Pro Thr Tyr Lys Ala Lys Pro Ser Tyr Pro
 1               5                  10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
     50                  55                  60

<210> SEQ ID NO 8
<211> LENGTH: 3
<212> TYPE: PRT
<213> ORGANISM: Artificial Sequence
<220> FEATURE:
<223> OTHER INFORMATION: physiologically active component

<400> SEQUENCE: 8

Arg Gly Asp
 1

<210> SEQ ID NO 9
<211> LENGTH: 4
<212> TYPE: PRT
<213> ORGANISM: Artificial Sequence
<220> FEATURE:
<223> OTHER INFORMATION: physiologically active component

<400> SEQUENCE: 9

Arg Gly Asp Ser
 1

<210> SEQ ID NO 10
<211> LENGTH: 4
<212> TYPE: PRT
<213> ORGANISM: Artificial Sequence
<220> FEATURE:
<223> OTHER INFORMATION: physiologically active component

<400> SEQUENCE: 10

Arg Gly Asp Cys
 1
```

```
<210> SEQ ID NO 11
<211> LENGTH: 4
<212> TYPE: PRT
<213> ORGANISM: Artificial Sequence
<220> FEATURE:
<223> OTHER INFORMATION: physiologically active component

<400> SEQUENCE: 11

Arg Gly Asp Val
1

<210> SEQ ID NO 12
<211> LENGTH: 10
<212> TYPE: PRT
<213> ORGANISM: Artificial Sequence
<220> FEATURE:
<223> OTHER INFORMATION: physiologically active component

<400> SEQUENCE: 12

Arg Gly Asp Ser Pro Ala Ser Ser Lys Pro
1               5                   10

<210> SEQ ID NO 13
<211> LENGTH: 5
<212> TYPE: PRT
<213> ORGANISM: Artificial Sequence
<220> FEATURE:
<223> OTHER INFORMATION: physiologically active component

<400> SEQUENCE: 13

Gly Arg Gly Asp Ser
1               5

<210> SEQ ID NO 14
<211> LENGTH: 6
<212> TYPE: PRT
<213> ORGANISM: Artificial Sequence
<220> FEATURE:
<223> OTHER INFORMATION: physiologically active component

<400> SEQUENCE: 14

Gly Arg Gly Asp Thr Pro
1               5

<210> SEQ ID NO 15
<211> LENGTH: 6
<212> TYPE: PRT
<213> ORGANISM: Artificial Sequence
<220> FEATURE:
<223> OTHER INFORMATION: physiologically active component

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial Sequence
<220> FEATURE:
<223> OTHER INFORMATION: physiologically active component

<400> SEQUENCE: 16

Gly Arg Gly Asp Ser Pro Cys
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: physiologically active component

<400> SEQUENCE: 17

Tyr Arg Gly Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: physiologically active component

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: physiologically active component

<400> SEQUENCE: 19

Trp Gln Pro Pro Arg Ala Arg Ile
1               5

<210> SEQ ID NO 20
<211> LENGTH: 12
<212> TYPE: PRT
<213> ORGANISM: Artificial Sequence
<220> FEATURE:
<223> OTHER INFORMATION: physiologically active component

<400> SEQUENCE: 20

Asn Arg Trp His Ser Ile Tyr Ile Thr Arg Phe Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: physiologically active component

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: physiologically active component

<400> SEQUENCE: 22

Lys Ala Phe Asp Ile Thr Tyr Val Arg Leu Lys Phe
1               5                   10

<210> SEQ ID NO 23
```

```
<211> LENGTH: 5
<212> TYPE: PRT
<213> ORGANISM: Artificial Sequence
<220> FEATURE:
<223> OTHER INFORMATION: physiologically active component

<400> SEQUENCE: 23

Ile Lys Val Ala Asn
1               5

<210> SEQ ID NO 24
<211> LENGTH: 16
<212> TYPE: PRT
<213> ORGANISM: Artificial Sequence
<220> FEATURE:
<223> OTHER INFORMATION: physiologically active component

<400> SEQUENCE: 24

Lys Lys Gln Arg Phe Arg His Arg Asn Arg Lys Gly Tyr Arg Ser Gln
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: physiologically active component

<400> SEQUENCE: 25

Val Ala Glu Ile Asp Gly Ile Gly Leu
1               5

<210> SEQ ID NO 26
<211> LENGTH: 10
<212> TYPE: PRT
<213> ORGANISM: Artificial Sequence
<220> FEATURE:
<223> OTHER INFORMATION: physiologically active component

<400> SEQUENCE: 26

Pro His Ser Arg Asn Arg Gly Asp Ser Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: physiologically active component

<400> SEQUENCE: 27

Asn Arg Trp His Ser Ile Tyr Ile Thr Arg Phe Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: physiologically active component

<400> SEQUENCE: 28

Thr Trp Tyr Lys Ile Ala Phe Gln Arg Asn Arg Lys
1               5                   10
```